United States Patent [19]

Acher et al.

[11] Patent Number: 5,116,857
[45] Date of Patent: May 26, 1992

[54] METHOD OF INCREASING GASTROINTESTINAL MOTILITY WITH SUBSTITUTED BENZAMIDES

[75] Inventors: Jacques Acher, Itteville; Jean-Claude Monier, Lardy; Jean-Paul Schmitt, Arpajon, all of France; Brenda Costall; Robert Naylor, both of Ilkey, United Kingdom; Renee Gardaix-Luthereau, Cachan, France

[73] Assignee: Laboratoires Delagrange Div. Societe d'Applications Pharmacodynamiques, Paris, France

[21] Appl. No.: 450,422

[22] Filed: Dec. 14, 1989

[30] Foreign Application Priority Data

Dec. 14, 1988 [FR] France ................. 88 16433

[51] Int. Cl.$^5$ .................. A61K 31/425; A61K 31/42; A61K 31/415
[52] U.S. Cl. ..................... 514/370; 514/374; 514/377; 514/385; 514/392; 514/395; 514/365
[58] Field of Search ............... 514/365, 370, 374, 377, 514/385, 392, 395

[56] References Cited

U.S. PATENT DOCUMENTS

| | | | |
|---|---|---|---|
| 3,177,252 | 4/1965 | Thominet | 564/176 |
| 4,267,175 | 5/1981 | Watts | 514/218 |
| 4,772,618 | 9/1988 | Vega-Noverola et al. | 514/326 |
| 4,835,172 | 5/1989 | Acher et al. | 514/392 |
| 4,870,074 | 9/1989 | Kon et al. | 514/233.8 |
| 4,877,780 | 10/1989 | Vega-Noverola et al. | 514/161 |
| 4,914,117 | 4/1990 | Acher et al. | 514/370 |

FOREIGN PATENT DOCUMENTS 0295350 12/1988 European Pat. Off.
3643103 6/1987 Fed. Rep. of Germany.
2592042 6/1987 France.

OTHER PUBLICATIONS

Chemical Abstracts (108:37828a) 1988.
Chemical Abstracts (111:146821a) 1989.
Katzung, Ed, Basic Clinical Pharmacology, 2d Ed., Lange Medical Publicaitons, p. 776 (1984).
R. A. Harrington, et al., "Metoclopramide an Updated Review of its Pharmacological Properties and Clinical Use," Drugs 25:451–462 (1983).
B. Cox et al., "Aphomorphine and Gastric Emptying in the Guinea Pig", Brit. J. Pharmacol. 70 (1980) 104P.

Primary Examiner—Frederick E. Waddell
Assistant Examiner—K. Weddington
Attorney, Agent, or Firm—Fitzpatrick, Cella, Harper & Scinto

[57] ABSTRACT

The present invention relates to the use of substituted benzamides of formula (1):

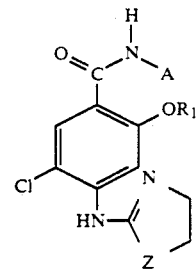

in which:
A is linear or branched $C_1$–$C_3$ alkyl; allyl or diethylaminoethyl;
$R_1$ is hydrogen or methyl, and
Z— is —NH—, —O— or —S—,
and of their pharmacologically acceptable salts for modifying gastric motility.

9 Claims, 1 Drawing Sheet

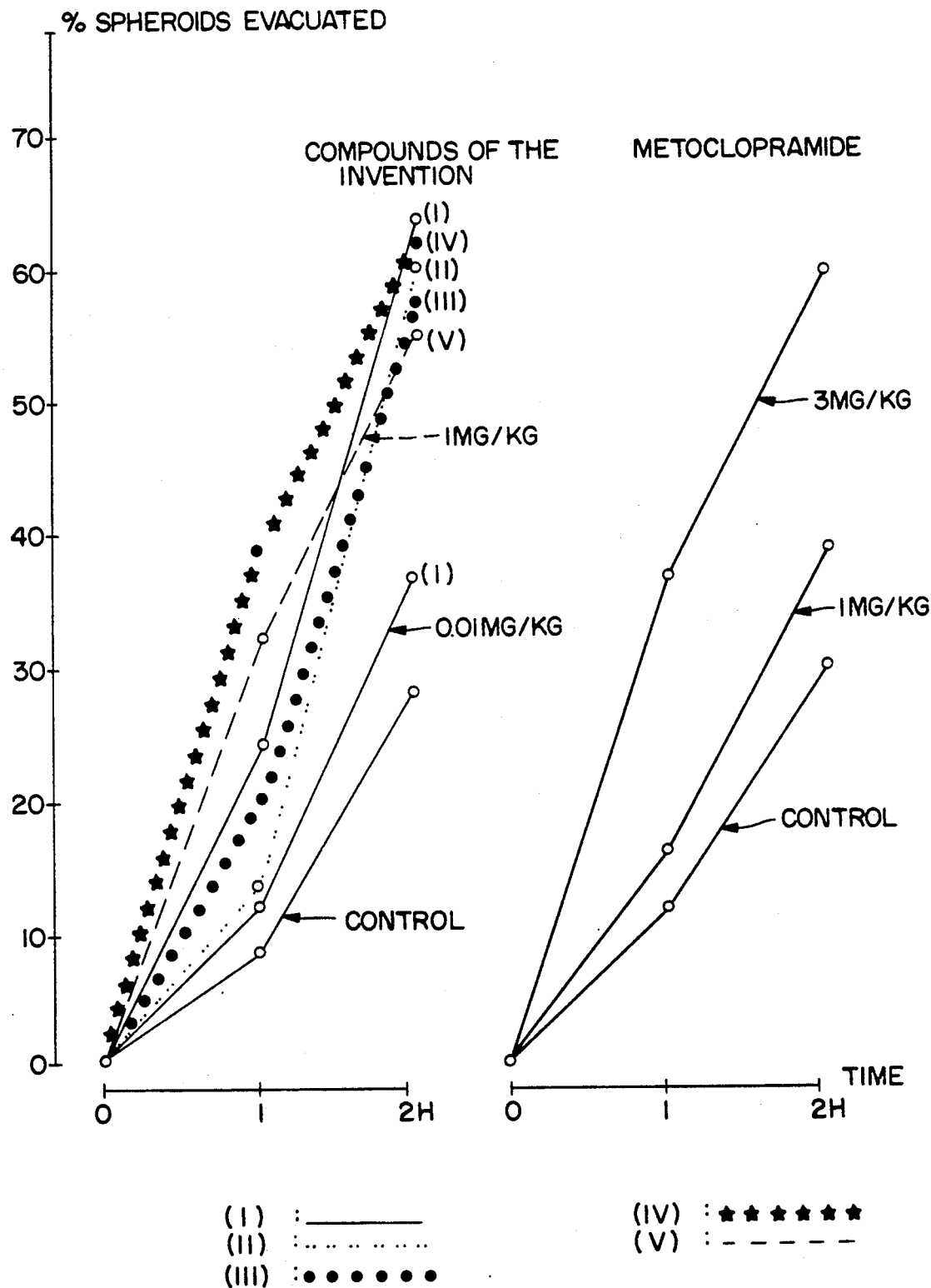

METHOD OF INCREASING GASTROINTESTINAL MOTILITY WITH SUBSTITUTED BENZAMIDES

BACKGROUND OF THE INVENTION

Gastrointestinal motility, or the ability of the gastrointestinal tract to move matter spontaneously, may be of beneficial therapeutic value for a variety of obvious reasons. For example, the gastrointestinal disruptions characteristic of conditions such as symptomatic gastroesophageal reflux and diabetic gastroparesis (diabetic gastric stasis) may result in symptoms which may be detrimental to the patient, such as nausea, vomiting, heartburn, persistent fullness after meals and anorexia. Such symptoms may be alleviated by increasing gastrointestinal motility, with consequent benefit to the patient. In addition, increased gastrointestinal motility may prevent the nausea and vomiting associated with emetogenic cancer therapy, may be used to facilitate small bowel intubulation and to stimulate gastric emptying and intestinal transit to facilitate radiological examination. Accordingly, chemical compounds that can increase gastrointestinal motility have been sought for use as pharmaceutical agents in the treatment of the associated symptoms. For example, the compound N-(2-diethylaminoethyl)-2-methoxy-4-amino-5-chlorobenzamide, known generically as metoclopramide, is disclosed in U.S. Pat. No. 3,177,252. This compound is commercially available and has been employed by physicians to increase gastrointestinal motility. Nevertheless, new agents that possess similar utility, or agents that are more potent that metoclopramide in increasing gastrointestinal motility, are desirable.

SUMMARY OF THE INVENTION

The present invention concerns the pharmaceutical uses of the compounds represented by the following chemical formula I:

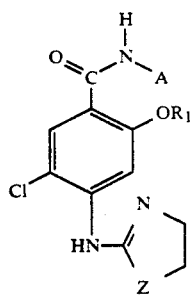

in which:
A is linear or branched $C_1$-$C_3$ alkyl; allyl or diethylaminoethyl;
$R_1$ is hydrogen or methyl and
Z is —NH—, —O— or —S—
and their pharmacologically acceptable salts.

The methods for preparation of the compounds of the invention are described in French Patent No. 2,592,042 and U.S. Pat. No. 4,835,172, issued May 30, 1989 to Acher, et al., the disclosures of which are incorporated herein by reference. In such citations the compounds are said to be useful as activators of the central nervous system and as antidepressants. New and extensive studies, however, have demonstrated that, in addition to their action on the central nervous system, the compounds of the invention increase gastrointestinal motility, which was not foreseeable from the properties previously mentioned.

In addition, such activity offers the advantage of leading to methods of improving gastrointestinal motility with compounds of greater potency than the conventionally used metoclopramide. The compounds may be administered in therapeutically effective amounts to patients, including lower animals and humans.

BRIEF DESCRIPTION OF THE DRAWINGS

FIG. 1 is a graph of a comparison of the activity of typical compounds of the invention with metoclopramide in increasing gastric emptying in the guinea pig.

DETAILED DESCRIPTION OF THE INVENTION

Typical compounds useful in the present invention include:
Compound I,
N-[2-(diethylamino)ethyl]-2-methoxy-4-[(4,5-dihydro-1H-imidazol-2-yl)-amino]-5-chlorobenzamide.
Compound II
N-[2-(diethylamino)ethyl]-2-methoxy-4-[(4,5-dihydro-2-thiazolyl)amino]-5-chlorobenzamide.
Compound III
N-[2-(diethylamino)ethyl]-2-methoxy-4-[(4,5-dihydro-2-oxazolyl)amino]-5-chlorobenzamide.
Compound IV
N-methyl-2-methoxy-4-[(4,5-dihydro-1H-imidazol-2-yl)amino] -5-chlorobenzamide.
Compound V
N-[2-(diethylamino)ethyl]-2-hydroxy-4-[(4,5-dihydro-1H-imidazol-2-yl)-amino]-5-chlorobenzamide.
Compound VI
N-ethyl-2-methoxy-4-[(4.5-dihydro-1H-imidazol-2-yl)amino]-5-chloro benzamide.
Compound VII
N-isopropyl-2-methoxy-4-[(4,5-dihydro-1H-imidazol-2-yl) amino]-5-chlorobenzamide.
Compound VIII
N-allyl-2-methoxy-4-[(4,5-dihydro-1H-imidazol-2-yl)amino]-5-chlorobenzamide.

The preparation of Compounds I, II, III, VII and VIII is disclosed in the above-incorporated U.S. Pat. No. 4,835,172 issued May 30, 1989 in Examples I, XXXVII, XXXIX, XXXVI and XXXV, thereof, respectively. The synthesis of Compounds IV, V and VI is illustrated as follows:

Synthesis of N-methyl-2-methoxy-4-[(4,5-dihydro-1H-imidazol-2-yl)amino]-5-chloro benzamide (Compound IV)

150 ml of methanol and 2.3 g of sodium are introduced into a 500-ml three-necked flask. When all the sodium has been consumed, 26.95 g of 2-methoxy-4-[(4,5-dihydro-1H-imidazol-2-yl)amino]-5-chlorobenzoic acid were added. Discussion takes place, followed by crystallization. The solvent was driven off to dryness under vacuum and the crystals were then ground and introduced into a 500-ml three-necked flask with 100 ml of chloroform. 22 ml of thionyl chloride were poured slowly into the suspension. Gaseous evolution took place and the temperature rose to 30° C. The mixture was heated for 2 hours to 50° C. and then cooled and the solvent was dried off. The residue was poured into 150 ml of 30% strength aqueous methylamine solution. After one hour's stirring, the product was drained, washed with water and dried at 70° C.

20.81 g of product (yield=73.7%) were obtained. 18.89 g of product were dissolved in 180 ml of water and 10 ml of acetic acid, treated with charcoal, filtered, precipitated with 25 ml of ammonia solution, drained, washed and dried at 70° C. 17.5 g of product were obtained. An impurity estimated at 3% and traces of ester were detected by NMR. 16.5 g of product were dissolved under reflux in 215 ml of dimethylformamide, treated with charcoal, filtered while hot, crystallized when cold, drained, washed with dimethylformamide and then with water and dried. 13 g of product still containing an impurity were obtained.

These 13 g were redissolved in 130 ml of water and 8 ml of acetic acid. The solution was filtered, and the precipitate obtained by adding 20 ml of ammonia solution was then drained, washed and dried at 70° C.

12.5 g of product (total yield=51.7%) were obtained. M.p. above 260° C.

Analysis: $H_2O$ : 0.5%; Assay (corrected) : 98.8%; Cl (corrected) : 12.63% (calculated: 12.54%); N (corrected) : 19.57% (calculated: 19.82%).

The NMR and IR spectra were compatible with the expected structure.

Synthesis of N-[2-(diethylamino)ethyl]-2-hydroxy-4-[(4,5-dihydro-1H-imidazol-2-yl) amino]-5-chloro-benzamide (Compound V)

Stage 1

N-[2-(diethylamino)ethyl]-2-hydroxy-4-isothio-cyano-5-chlorobenzamide hydrochloride 57 g of N-[2-(diethylamino)ethyl]-2-hydroxy-4-amino-5-chlorobenzamide and 300 ml of carbon tetrachloride were introduced into a 1-liter three-necked flask equipped with a stirrer, a thermometer, a condenser and a dropping funnel, and a solution of 20 ml of thiophosgene in 100 ml of carbon tetrachloride was then added.

The mixture was brought to reflux for 3 hours with stirring and a solution of 8 ml of thiophosgene in 50 ml of carbon tetrachloride was then added. The mixture was left for a further 4 hours under reflux and then cooled to 15° C., and the product was drained washed twice with 50 ml of carbon tetrachloride and then three times with 50 ml of acetone and dried. 68.63 g of product (yield=94%) were obtained. M.p. 153° C.

Stage 2

N-[2-(diethylamino)ethyl]-2-hydroxy-4-[N'-(2-aminoethyl)thioureido]-5-chlorobenzamide 36.4 g of N-[2-(diethylamino)ethyl]-2-hydroxy-4-isothiocyanato-5-chlorobenzamide hydrochloride, 200 ml of methylene chloride and 10 g of triethylamine were introduced into a beaker with stirring. The mixture was stirred for 15 minutes and the salts formed were then filtered off.

The filtrate was poured with stirring, in the course of 40 minutes, into a three-necked flask containing 15 g of ethylenediamine and 200 ml of isopropyl ether, the temperature being maintained below −10° C. The mixture was stirred for 3 hours while the temperature was allowed to rise, and the precipitate was then filtered off. This precipitate was reintroduced into the flask. 200 ml of water were added, the mixture was stirred for 1 hour and the product was drained, washed with water and dried at 40° C. 34.52 g of product (yield=89%) were obtained. M.p.=instantaneous decomposition at about 160°–170° C., the melting point then decreasing.

Stage 3

N-[2-(diethylamino)ethyl]-2-hydroxy-4-[(4,5-dihydro-1H-imidazol-2-yl) amino]-5-chlorobenzamide 62 g of N-[2-(diethylamino)ethyl]-2-hydroxy-4-[N'-(2-aminoethyl) thioureido]-5-chlorobenzamide and 500 ml of ethyl carbonate were introduced into a 1-liter three-necked flask equipped with a stirrer, a thermometer and a condenser.

The mixture was brought to reflux for 2 hours in an oil bath at 155°–160° C. Vegetable charcoal was added, the mixture was left under reflux for a further 10 minutes and filtered while hot and the filter was washed twice with 50 ml of hot ethyl carbonate.

The product was collected in a breaker with stirring. As cooling began, a grey gum adhered to the walls. The mass was transferred while still hot to another beaker and cooled to −10° C. with stirring.

The precipitate was drained, washed and stirred to a paste with 4×50 ml of petroleum ether, then dried. 25.25 g of product containing impurities were obtained.

24.8 g of product and 225 ml of butyl acetate were brought to reflux for 10 minutes. The mixture was cooled to 0°–5° C. and the product was drained, washed and stirred to a paste with 4×50 ml of isopropyl ether, then dried. 17.5 g of product still containing an impurity were obtained. 17 g of product were taken up under reflux in 85 ml of butyl acetate, cooled to 5° C., drained, washed and stirred to a paste with 4×40 ml of isopropyl ether and then dried.

15.32 g of product were obtained. 9.6 g of product were dissolved under reflux in 300 ml of ethyl carbonate. The solution was treated with charcoal and then filtered. The crystals formed in the cold were drained, washed with ethyl ether and dried at 60° C. under vacuum, then for 72 hours at 80° C. under vacuum.

6 g of product (total yield=17.7%) were obtained. M.p. 151° C.; m.p. 205° C. when recrystallized.

Analysis: Cl : 10.27% (calculated: 10.02); Assay : 96%.

The NMR spectrum was compatible with the expected structure.

Synthesis of N-ethyl-2-methoxy-4-[(4,5-dihydro-1H-imidazol-2-yl)amino]-5-chlorobenzamide (compound VI)

56.7 g of methyl 2-methoxy 4-[(4,5-dihydro-1H-imidazol-2-yl)amino]-5-chlorobenzoate, 100 ml of ethylene glycol and 200 ml of a 60% aqueous ethylamine solution were introduced in a 500 ml three-necked flask equipped with a stirrer, a thermometer and a condenser. The mixture was heated for 120 hours at 75° C. with stirring and 10 ml of soda lye was then added. The mixture was stirred for a further hour, then cooled.

42.5 g of product (yield : 72%) were obtained, which were recrystallized in 512 ml of methanol. The precipitate was drained, washed with methanol and dried at 75°–80° C.

38.2 g of product were obtained, which were dissolved in 400 ml of water and acetic acid. The solution was filtered and the precipitate obtained by addition of ammonia solution was left to crystallize overnight in a refrigerator. The crystals were drained, washed with water and dried under vacuum on phosphorus pentoxide at 70° C.

34.5 g of product (yield of purification = 80.7%) were obtained M.p. = 237° C.

The NMR and IR spectra were compatible with the expected structure.

The increased gastrointestinal motility achieved by the methods of this invention has been demonstrated in standard laboratory animals. The following experimental protocol was observed in vivo in the guinea pig, in order to compare the action of the compounds of the invention with that of metaclopramide, a reference product in this field.

Feeding of the animals were interrupted 14 hours before measurement of gastric emptying. The experimentation was conducted under weak illumination, with the least possible noise and disturbances, solely by experimentors having daily contact with the guinea pigs and having sufficient initial training in handling the animals. The animals were then subjected to minimal stress.

The measurement of gastric emptying was carried out by x-ray localization (50 KV, 30 mA, 0.5-0.8 s.), on Kodak plates (NS-2T, 13×18 cm) of barium sulfate spheroids (approximately 30, 1 mm in diameter) coated with polystyrene, which the guinea pigs were made to swallow by placing them in the back of the throat, in a solution of 0.2 ml of 1% carboxymethylcellulose with 0.05 ml of glycerine, so as to initiate rapid and voluntary deglutition.

The passage of the spheroids was followed for 3 to 4 hours, the animals being placed in their customary cages for that time and taken out only 5 minutes before x-ray exposure (at intervals of 30-60 minutes). During the x-ray procedure, the animals were placed in individual holding cages, keeping them comfortably in a stable position, the cage being sufficiently sized (33×15 cm and 13 cm high) so as to comfortably maintain a 450 to 550 gram guinea pig between the padded walls, the animal being trained to enter the cage and remain there tranquilly and without stress.

Gastric emptying was measured by the number of spheroids leaving the stomach. For each dose of product studied, 6 guinea pigs were used, and the responses were compared to those of guinea pigs receiving the appropriate vehicle.

Compound (I) was studied at doses of 1 mg/kg and 0.01 mg/kg, Compounds (II) to (V) were studied at a dose of 1 mg/kg, the compounds (VI) to (VIII) at a dose of 5 mg/kg. Metoclopramide was evaluated at doses of 1 mg/kg and 5 mg/kg.

The results are recorded in graphic form in FIG. 1. The compounds according to the invention and metoclopromide were dissolved in distilled water and the doses are expressed as base.

Administration intraperitoneally of metoclopramide and the compounds according to the invention caused an increase in gastric emptying as illustrated in FIG. 1 in immobilized guinea-pigs.

This emptying is expressed, in FIG. 1 and Table 1, as a percentage of spheroids leaving the stomach.

TABLE 1

Gastric emptying as a function of time, in guinea-pigs, after i.p. administration of 1 mg/kg of compound

| Compound | After 1 hour | After 2 hours |
| --- | --- | --- |
| I | 24 | 63 |
| II | 12.5 | 60 |
| III | 20 | 57 |
| IV | 38 | 62 |
| V | 32 | 55 |

TABLE 1-continued

Gastric emptying as a function of time, in guinea-pigs, after i.p. administration of 1 mg/kg of compound

| Compound | After 1 hour | After 2 hours |
| --- | --- | --- |
| metoclopramide | 16 | 39 |

From the results obtained, it is clear that gastric emptying is significantly increased in comparison with control groups. Compounds (I) to (V) at a dose of 1 mg/kg induced a gastric emptying of 55 to 63% after 2 hours, whereas that of the control group was only 28%. Compounds (VII) and (VIII), administered at a dose of 5 mg/kg, induced a gastric emptying of 46.2 and 47.4%, respectively, after 2 hours, whereas that of the control group was only 24.8%.

Furthermore, from the tests conducted, it is apparent that the compounds according to the invention are more potent than metoclopramide. It was found, for example, that, at a dose of 1 mg/kg of the compounds (I) and (IV) under study, a result equivalent to the use of 5 mg/kg of metoclopramide was obtained.

The acute toxicity of the compounds of the invention administered intravenously was studied in male mice. The following median lethal doses ($LD_{50}$) were determined as shown in Table 2:

TABLE 2

| Compound | $LD_{50}$ in mg/kg |
| --- | --- |
| I | 12.8-14.4 |
| II | 40.6-48.7 |
| III | 91-116 |
| IV | 95.8-138 |
| V | 65.7-76.7 |
| metoclopramide | 25.4-37.9 |

The compounds of the invention can be administered in any number of conventional pharmaceutical forms, including, but not limited to, tablets, capsules, pills, syrups, injectable solutions or other common dosage forms intended for oral, parenteral or any other conventional pharmaceutical administration, in combination with solid or liquid excipients. Substances which are inert relative to the compounds can be used in these preparations, such as lactose, magnesium stearate, starch, talc, cellulose, levillite, alkali metal lauryl-sulphates, saccharose and other vehicles commonly employed in pharmaceutical preparations.

By way of illustration only, the compounds may be formulated in tablet dosage form as shown below. As the formulation is provided for illustrative purposes only, it is understood that the invention is not restricted or limited thereto, as the scope of the invention is defined and restricted or limited solely as set forth in the appended claims.

| | |
| --- | --- |
| N-[2-(diethylamino)-ethyl]-2-methoxy-4-[(1-H-4,5-dihydro-2-oxazolyl)-amino]-5-chlorobenzamide | 100 mg |
| dried starch | 20 mg |
| lactose | 100 mg |
| methylcellulose 1500 cps | 1.5 mg |
| levilite | 10 mg |
| magnesium stearate | 4 mg |

What is claimed is:

1. A method for increasing gastrointestinal motility which comprises administering a therapeutically effective amount of a compound of the general formula I:

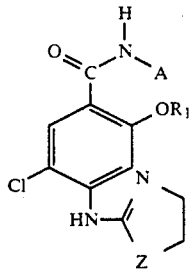

(I)

in which:

A is linear or branched $C_1$–$C_3$ alkyl; allyl or diethylaminoethyl;

$R_1$ is hydrogen or methyl, and

Z— is —NH—, —O— or —S—, or their pharmacologically acceptable salts, to an appropriate host.

2. The method according to claim 1 employing N-[2-(diethylamino)-ethyl]-2-methoxy-4-[(4,5-dihydro-1H-imidazol-2-yl)amino]-5-chlorobenzamide.

3. The method according to claim 1 employing N-[2-(diethylamino)-ethyl]-2-methoxy-4-[(4,5-dihydro-2-thiazolyl) amino]-5-chlorobenzamide.

4. The method according to claim 1 employing N-[2-(diethylamino)-ethyl]-2-methoxy-4-[(4,5-dihydro-2-oxazolyl)amino] -5-chlorobenzamide.

5. The method according to claim 1 employing N-methyl-2-methoxy-4-[(4,5-dihydro-1H-imidazol-2-yl)amino]-5-chlorobenzamide.

6. The method according to claim 1 employing N-[2-(diethylamino)-ethyl]-2-hydroxy-4-[(4,5-dihydro-1H-imidazol-2-yl) amino]-5-chlorobenzamide.

7. The method according to claim 1 employing N-ethyl-2-methoxy-4-[(4,5-dihydro-1H-imidazol-2-yl)amino]-5-chlorobenzamide.

8. The method according to claim 1 employing N-isopropyl-2-methoxy-4-[(4,5-dihydro-1H-imidazol-2-yl)amino]-5-chlorobenzamide.

9. The method according to claim 1 employing N-allyl-2-methoxy-4-[(4,5-dihydro-1H-imidazol-2-yl)amino]-5-chlorobenzamide.

* * * * *

UNITED STATES PATENT AND TRADEMARK OFFICE
CERTIFICATE OF CORRECTION

PATENT NO. : 5,116,857
DATED : May 26, 1992
INVENTOR(S) : JACQUES ACHER, ET AL.

It is certified that error appears in the above-identified patent and that said Letters Patent is hereby corrected as shown below:

IN [57] ABSTRACT

Line 7, "Z-" should read -- -Z- --.

COLUMN 2

Line 57, "Discussion" should read --Dissolution--.

COLUMN 3

Line 31, "-cyano-" should read -- -cyanato- --.
Line 44, "drained" should read --drained,--.

COLUMN 5

Line 10, "metaclopramide" should read --metoclopramide--.

COLUMN 7

Line 21, "Z-is" should read -- - Z- is--.

Signed and Sealed this

Seventeenth Day of August, 1993

BRUCE LEHMAN

Attest:

Attesting Officer

Commissioner of Patents and Trademarks